(12) United States Patent
Bates

(10) Patent No.: US 7,244,444 B2
(45) Date of Patent: Jul. 17, 2007

(54) GRAFT MATERIAL, STENT GRAFT AND METHOD

(75) Inventor: Brian L. Bates, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/093,759

(22) Filed: Mar. 30, 2005

(65) Prior Publication Data

US 2005/0220848 A1 Oct. 6, 2005

Related U.S. Application Data

(60) Provisional application No. 60/558,667, filed on Mar. 31, 2004, provisional application No. 60/558,794, filed on Mar. 31, 2004.

(51) Int. Cl.
*A61K 31/74* (2006.01)
*A61K 9/70* (2006.01)

(52) U.S. Cl. .................. 424/423; 424/78.17; 424/400; 424/443

(58) Field of Classification Search ............. 424/78.17, 424/423, 400, 443, 399; 435/399, 400, 443
See application file for complete search history.

(56) References Cited

U.S. PATENT DOCUMENTS

| | | |
|---|---|---|
| 2,127,903 A | 8/1938 | Bowen |
| 3,772,137 A | 11/1973 | Tolliver |
| 3,953,566 A | 4/1976 | Gore |
| 4,473,665 A | 9/1984 | Martini-Vvedensky |
| 4,502,159 A | 3/1985 | Woodroof |
| 4,675,361 A | 6/1987 | Ward, Jr. |
| 4,861,830 A | 8/1989 | Ward, Jr. |
| 4,902,508 A | 2/1990 | Badylak et al. |
| 4,956,178 A | 9/1990 | Badylak et al. |
| 5,017,664 A | 5/1991 | Grasel et al. |
| 5,024,671 A | 6/1991 | Tu et al. |
| 5,037,377 A | 8/1991 | Alonso |
| 5,160,674 A | 11/1992 | Colton et al. |
| 5,275,826 A | 1/1994 | Badylak et al. |
| 5,281,422 A | 1/1994 | Badylak et al. |
| 5,516,533 A | 5/1996 | Badylak et al. |
| 5,554,389 A | 9/1996 | Badylak et al. |
| 5,589,563 A | 12/1996 | Ward et al. |
| 5,711,969 A | 1/1998 | Patel et al. |
| 5,733,337 A | 3/1998 | Carr, Jr. et al. |
| 5,980,799 A | 11/1999 | Martakos et al. |
| 6,206,931 B1 | 3/2001 | Cook et al. |
| 6,264,992 B1 | 7/2001 | Voytik-Harbin et al. |
| 6,358,284 B1 | 3/2002 | Fearnot et al. |
| 6,379,710 B1 | 4/2002 | Badylak |
| 6,547,815 B2 | 4/2003 | Myers |
| 6,666,892 B2 | 12/2003 | Hiles et al. |
| 6,702,849 B1 | 3/2004 | Dutta et al. |
| 2002/0099448 A1 | 7/2002 | Hiles et al. |
| 2002/0187288 A1 | 12/2002 | Lim et al. |
| 2002/0198587 A1 | 12/2002 | Greenberg et al. |
| 2003/0026787 A1 | 2/2003 | Fearnot et al. |
| 2003/0114917 A1 | 6/2003 | Holloway et al. |
| 2003/0149471 A1 | 8/2003 | Briana et al. |
| 2004/0082989 A1 | 4/2004 | Cook et al. |
| 2004/0180042 A1 | 9/2004 | Cook et al. |
| 2005/0113905 A1* | 5/2005 | Greenberg et al. ......... 623/1.16 |
| 2005/0149166 A1* | 7/2005 | Schaeffer et al. .......... 623/1.13 |
| 2005/0171598 A1* | 8/2005 | Schaeffer ................... 623/1.35 |
| 2005/0222668 A1* | 10/2005 | Schaeffer et al. .......... 623/1.13 |

FOREIGN PATENT DOCUMENTS

| | | |
|---|---|---|
| WO | WO 98/22158 | 5/1998 |
| WO | WO 98/25636 | 6/1998 |
| WO | WO 98/25637 | 6/1998 |
| WO | WO 98/26291 | 6/1998 |
| WO | WO 98/53761 | 12/1998 |
| WO | WO 02/30329 | 4/2002 |
| WO | WO 03/002165 | 1/2003 |
| WO | WO 2004/022107 | 3/2004 |

OTHER PUBLICATIONS

International Standards Organization (ISO) Standard No. 10993 (U.S. Pharmacopeia (USP) 23).
U.S. Food and Drug Administration (FDA) blue book memorandum No. G95-1, entitled "Use of International Standard ISO-10993, Biological Evaluation of Medical Devices Part-1: Evaluation and Testing".
Hodde, Tissue Engineering 8(2):295-308 (2002).

(Continued)

*Primary Examiner*—Ruth A Davis
(74) *Attorney, Agent, or Firm*—Brinks Hofer Gilson & Lione

(57) ABSTRACT

This invention is directed to graft materials for implanting, transplanting, replacing, or repairing a part of a patient and to methods of making the graft materials. The present invention is also directed to stent grafts and endoluminal prostheses formed of the graft materials. More specifically, the present invention is a graft material which includes polymeric sheet comprising holes. The graft material also comprises an ECM disposed in the holes of the polymeric sheet. The polymeric sheet of the graft material could be a textile or a porous polymer.

17 Claims, 6 Drawing Sheets

OTHER PUBLICATIONS

Huynh et al., 17 Nature Biotechnology 1083 (Nov. 1999).
Medalie et al., ASAIO J. 42:M455 (1996).
Isch et al., J. Pediatr. Surg. 36:266 (2001).
Chaplin et al., Neurosurgery 45:320 (1999).
Inoue et al., J. Reconstr. Microsurg. 12:307 (1996).
Walden et al., Ann. Plast. Surg. 45:162 (2000).
Vecchia et al., J. Pediatr. Surg. 34:167(1999).
Carbone et al., J. Urol. 165:1605 (2001).
Meezan et al, Life Sci. 17:1721 (1975).
Badylak et al., J. Pediatr. Surg. 35:1097 (2000).
Merguerian et al., BJU Int. 85:894 (2000).
Wefer et al., J. Urol. 165:1755 (2001).
Reddy et al., J. Urol. 164:936 (2000).
Aplin et al., J. Cell Sci. 79:119 (1985).
Lei et al., Biol. Reprod. 60:176 (1999).
Meinert et al., J. Obstet. Gynecol. 184:679 (2001).
Avila et al., Cornea 20:414 (2001).
Young et al., Fertil. Steril. 55:624 (1991).
Dietrich, *J. Invasive Cardiol.* 13(5):383-390, 2001.

* cited by examiner

GRAFT MATERIAL, STENT GRAFT AND METHOD

RELATED APPLICATIONS

The present patent document claims the benefit of the filing date under 35 U.S.C. §119(e) of Provisional U.S. patent application Ser. No. 60/558,667, filed Mar. 31, 2004; and Provisional U.S. patent application Ser. No. 60/558,794, filed Mar. 31, 2004, disclosures of which are hereby incorporated by reference.

TECHNICAL FIELD

This invention is directed to graft materials for implanting, transplanting, replacing, or repairing a part of a patient and to methods of making the graft materials. The present invention is also directed to stent grafts and endoluminal prostheses formed of the graft materials.

BACKGROUND

Identification of materials suitable for grafts can be difficult, because such materials must possess disparate properties. For example, vascular graft materials should exhibit mechanical stability under continuous stress, should have compliance similar to that of the host tissue, and should be nonthromogenic. In some applications, graft materials may also provide for endothelialization and have sufficient porosity to allow for capillarization. Other preferred properties of graft materials include being non-allergenic and non-carcinogenic. While all of these properties may be specifically designed into a material, it is also desirable for the material to be inexpensive to fabricate.

Portions of the human vasculature may be replaced or treated with synthetic vascular grafts. One typical area of application includes the replacement or treatment of blood vessels with vascular grafts. Synthetic vascular grafts may have wide variety of configurations and may be formed from a wide variety of materials. Conventional vascular graft implants include those which are formed from a biologically compatible material which retains an open lumen to permit blood to flow through the synthetic graft after implant. Polymeric structures typically used for vascular graft and stent procedures may include woven and non-woven textiles and porous polymer sheets.

SUMMARY

In one embodiment, the present invention is a graft material which includes polymeric sheet comprising holes. The graft material also comprises an extracellular collagen matrix (ECM) disposed in the holes of the polymeric sheet. The polymeric sheet of the graft material could be a textile or a porous polymer. The textile includes fibers and may take many forms, including woven (including knitted) and non-woven. Preferably, the fibers of the textile comprise a synthetic polymer. More preferably the textile is a polyester such as polyethylene terephthalate. The porous polymer may be formed from polyesters, fluorinated polymers, polysiloxanes, polyurethanes, polyolefins, polyacrylonitrile, nylons, polyaramids and polysulfones. Preferably, the polymeric sheet further comprises a polyetherurethane urea and a surface modifying agent comprising a siloxane. Preferably, the ECM is a small intestine submucosa. More preferably, the small intestine submucosa is a comminuted small intestine submucosa, which may be fluidized or in a powder form before introduction into the holes.

In another embodiment, the present invention is an endoluminal prosthesis, comprising a tubular graft material which includes a polymeric sheet comprising holes; and an ECM disposed in the holes of the polymeric sheet. The endoluminal prosthesis also includes a stent disposed about the graft material. Preferably, the ECM is a small intestine submucosa. Preferably, the small intestine submucosa is a comminuted small intestine submucosa. The prosthesis may be a bifurcated prosthesis. The graft material of this endoluminal prosthesis may include a single proximal opening and two distal openings. The endoluminal prosthesis may further comprise a stent connected to and extending from the proximal opening. The stent of the endoluminal prosthesis may be a self-expanding stent or balloon expandable stent. The endoluminal prosthesis may further include a plurality of stents.

In yet another embodiment, the present invention is a method of making a graft material for implantation. The method includes providing a polymeric sheet having holes. The method also includes providing an ECM and introducing the ECM into the holes wherein the ECM remains in the holes until after implantation. Preferably, the ECM is a small intestine submucosa. Preferably the small intestine submucosa is comminuted small intestine submucosa. The small intestine submucosa may be mechanically comminuted or enzymatically comminuted. The step of providing the comminuted small intestine submucosa comprises fluidizing the comminuted small intestine submucosa. Preferably fluidizing comprises adjusting the viscosity of the fluidized small intestine submucosa from about 2 to about 300,000 cps at 25° C. The introducing comprises immersing the polymeric sheet in the fluidized small intestine submucosa. The step of providing the comminuted small intestine submucosa comprises providing the comminuted small intestine submucosa in a form of a powder. The introducing comprises depositing a layer of the ECM onto at least one side of the polymeric sheet by, for example, dipping, spraying or painting the polymeric sheet with the ECM. The introducing comprises contacting one side of the polymeric sheet with the ECM, and applying a vacuum to the opposite side of the polymeric sheet. The introducing also comprises immobilizing the ECM within the holes by contacting the graft material with glutaraldehyde. The ECM may comprise a photoinitiator, and the immobilizing comprises exposing the graft material to a light source. The step of introducing further comprises drying the graft material.

DETAILED DESCRIPTION

Figure 1:
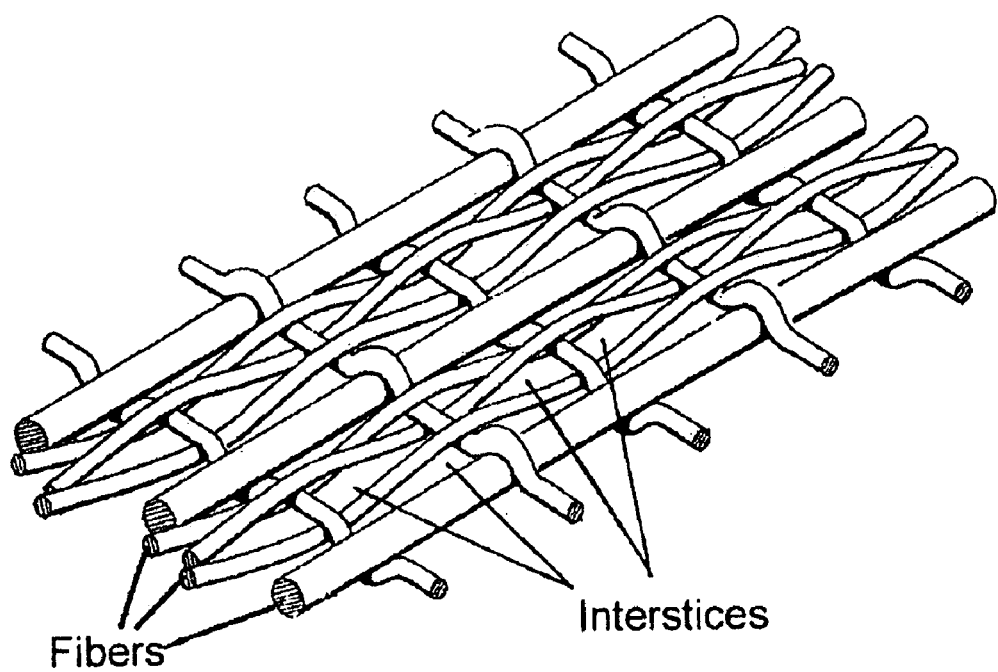
FIG. 1 is a schematic illustration of a fragmentary, perspective view of a single layer of woven fabric showing an exemplary distribution of filaments.

The present invention relates to graft materials containing a polymeric sheet impregnated with an extracellular collagen matrix material. Polymeric sheet may be a woven or non-woven textile or a porous polymer, such as polyester, fluorinated polymer, polysiloxane, polyurethane, polyolefin, polyacrylonitrile, nylon, polyaramid or polysulfone. Graft textiles include fibers and holes between the fibers, and the extracellular matrix material may be disposed in the holes. Porous polymer sheets include plurality of pores or holes, and the extracellular collagen matrix may be disposed in the holes. The graft materials may provide improvements in adhesion to and treatment of bodily tissues.

Unless defined otherwise, all technical and scientific terms used herein have the same meaning as commonly understood to one of ordinary skill in the art to which this invention belongs.

The term "graft" means any replacement for a bodily tissue or for a function of the bodily tissue. A graft may be transplanted from a donor to a recipient to repair a part of a body, and in some cases the patient can be both donor and recipient. For example, a graft may replace tissue that has been destroyed or create new tissue where none exists.

The term "sheet" means a monolithic layer of material. As used herein, the term "sheet" does not imply any particular shape, but includes flat layers, tubes, or other thin shaped objects. As used herein, the term "sheet" specifically includes textile materials formed from individual fibers, such as knitted or woven textiles or nonwoven textiles; and porous polymer sheets, formed from polyesters, fluorinated polymers, polysiloxanes, polyurethanes, polyolefins, polyacrylonitrile, nylons, polyaramids and polysulfones. The term "polymeric sheet" means a monolytic layer of textile or porous polymer material. The term "porous sheet" means a cohesive layer of material containing holes, such as small interstices pores.

The term "holes" means spaces that intervene between parts of the polymeric material. Holes include interstices, pores, cavities, apertures, and spaces. For example, holes, such as interstices are between fibers of the textile material.

The term "tissue" refers to an aggregation of similarly specialized cells united in the performance of a particular function. The term "tissue" encompass all types of biological tissue, including both hard and soft tissue, connective tissue (e.g., hard forms such as osseous tissue or bone), as well as other muscular or skeletal tissue.

The term "filament" refers to a long fiber. In this specification, it generally refers to a long, single fiber of the textile. The term filament or fiber encompasses fibers, yarns, threads, filaments and the like.

The term "maximum interstices spacing" refers to the longest distance between two fiber portions of the textile.

The terms "biodegradable" and "bioerodible" refers to something, such graft material, implant, coating, or dressing, that when placed the in vivo environment of its intended use will eventually dissolute into constituent parts that may be metabolized or excreted, under the conditions normally present in a living tissue. In exemplary embodiments, the rate and/or extent of biodegradation or bioerosion may be controlled in a predictable manner.

The term "endoluminal" refers to or describes objects that can be placed inside a lumen in a human or animal body. A lumen can be an existing lumen or a lumen created by surgical intervention. This includes lumens such as blood vessels, parts of the gastrointestinal tract, ducts such as bile ducts, parts of the respiratory system, etc. "Endoluminal device" of "endoluminal prosthesis" thus describes devices that can be placed inside one of these lumens.

The term "tubular" refers to the general shape of an endoluminal device which allows the module to carry fluid along a distance or fit within a tubular structure such as an artery. Tubular prosthetic modules include both branched and bifurcated modules.

The term "stent" refers to any device or structure that adds rigidity, expansion force or support to a prosthesis. The stent may be coated with a polymeric material by immersion in molten polymer or any other method known to one of skill in the art.

The term "stent graft" refers to a type of endoluminal prosthesis made of a tubular material and supported by at least one stent.

The term "healing" means replacing, repairing, healing, or treating of damaged or diseased tissues of a patient's body.

The terms "patient," "subject," and "recipient" as used in this application refer to any mammal, especially humans.

Fabric Structures

Graft materials may include textiles of a biocompatible material. The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Examples of biocompatible materials from which graft textiles can be formed include polyesters, such as poly (ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a graft textile material, provided the final textile is biocompatible. Polymeric materials that can be formed into fibers suitable for making textiles include polyethylene, polypropylene, polyaramids, polyacrylonitrile, nylons and cellulose, in addition to polyesters, fluorinated polymers, and polyurethanes as listed above. Preferably the textile is made of one or more polymers that do not require treatment or modification to be biocompatible. More preferably, the textile is made of a biocompatible polyester. Examples of biocompatible polyesters include DACRON (DUPONT, Wilmington, Del.) and TWILLWEAVE MICREL (VASCUTEK, Renfrewshire, Scotland).

Textile materials may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs that have been formed by knitting or weaving. The woven textile structure may be any kind of weave including, for example, a plain weave, a herringbone weave, a satin weave, or a basket weave. Referring to FIG. 1, a textile material contains fibers and interstices between the fibers.

In one example of woven textiles, knitted textiles include weft knit and warp knit fiber arrays. Weft knit fabric structures (including double-knit structures) utilize interlocked fiber loops in a filling-wise, or weft, direction, while warp knit structures utilize fabric loops interlocked in a length wise, or warp, direction. Weft knit structures generally are more elastic than warp knit structures, but the resiliency of warp knit fabrics is satisfactory to provide a substantial degree of elasticity, or resiliency, to the fabric structure without substantially relying on tensile fiber elongation for such elasticity. Weft knit fabrics generally have two dimensional elasticity (or stretch), while warp knit fabrics generally have unidirectional (width wise) elasticity. The different elasticity properties of the various knit or woven structures may be beneficially adapted to the functional requirement of the particular graft material application. In some cases, where little elasticity is desired, the fabric may be woven to minimize in plane elasticity but yet provide flexibility. For large diameter vascular grafts (6 mm diameter or larger) and various reconstructive fabric applications, polyethylene terephtalate fiber fabric arrays of suitably small fiber size may be utilized as materials for subsequent impregnation with the extracellular collagen matrix. Commercially available woven and knitted fabrics of medical grade Dacron fibers including, single and double velour graft fabrics, stretch Dacron graft fabric and Dacron mesh fabrics, provided the fibers that have suitably small diameter and other properties to provide graft materials in accordance with the present invention. For smaller vascular graft applications (less than 6 mm diameter), and for other applications for which suitable substrates of desired structure are not commercially available, special manufacture may be necessary.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, by Tolliver, disclosure of which is incorporated by reference. Fibers similar to those described are currently being manufactured by the DuPont Company from polyethylene terephthalate (often known as "DACRON™" when manufactured by DuPont), and by other companies from various substances. Certain physical parameters may be used to characterize the textile fibers used in a graft material. The fibers may have a tensile strength of at least about 20,000 psi and a tensile modulus of at least about $2\times10^6$ psi. Preferably, the textile is made of medical grade synthetic polymeric materials. The fibers of the textile may also have a high degree of axial orientation. The fibers may be of diameter from about 1 micron to about 5 millimeters. The denier of the textile may be from 0.5 denier per filament to 5 denier per filament. Preferably the interstices between the fibers of the textile comprise a maximum interstices spacing from about 1 micron to about 400 microns. More preferably, the interstices between the fibers of the textile comprise a maximum interstices spacing from about 1 micron to about 100 microns. Most preferably, the interstices between the fibers of the textile comprise a maximum interstices spacing from about 1 micron to about 10 microns.

Preferred textiles include those formed from polyethylene terephthalate and PTFE. These materials are inexpensive, easy to handle, have good physical characteristics and are suitable for clinical application.

In textile graft materials, the fibers provide a flexible array in sheet or tubular form so that the graft material is provided with a predetermined high degree of flexibility of the graft material which also has beneficial biologically compatible properties of extracellular collagen matrix. Furthermore, a high degree of elasticity may be provided through bending of the fibers of the array rather than through substantial tensile elongation of the fibers.

Preferred textile graft materials are made of woven polyester having a twill weave and a porosity of about 350 ml/min/cm$^2$ (available from VASCUTEK® Ltd., Renfrewshire, Scotland, UK).

Porous Polymer Sheets

Graft materials may also include porous polymer sheet of a biocompatible material.

Examples of biocompatible polymers from which porous sheets can be formed include polyesters, such as poly (ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible. More preferably, the porous sheet includes a biocompatible polyurethane. Examples of biocompatible polyurethanes include THORALON (THORATEC, Pleasanton, Calif.), BIOSPAN, BIONATE, ELASTHANE, PURSIL and CARBOSIL (POLYMER TECHNOLOGY GROUP, Berkeley, Calif.).

Preferably the porous polymeric sheet contains the polyurethane THORALON. As described in U.S. Patent Application Publication No. 2002/0065552 A1, incorporated herein by reference, THORALON is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A porous polymeric sheet can be formed from these two components by dissolving the base polymer and additive in a solvent such as dimethylacetamide (DMAC) and solidifying the mixture by solvent casting or by coagulation in a liquid that is a non-solvent for the base polymer and additive.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

In addition to THORALON, other polyurethane ureas may be used as a porous sheet. For example, the BPS-215 component with a MDI/PTMO mole ratio ranging from about 1.0 to about 2.5 may be used. Such polyurethane ureas preferably include a soft segment and include a hard segment formed from a diisocyanate and diamine. For example, polyurethane ureas with soft segments such as polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN—R—NCO, where —R— may be aliphatic, aromatic, cycloaliphatic or a mixture of aliphatic and aromatic moieties. Examples of diisocyanates include tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanat-e, 1-methoxyphenyl 2,4-diisocyanate, 4,4'-biphenylene diisocyanate, 3,3-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

In addition to polyurethane ureas, other polyurethanes, preferably those having a chain extended with diols, may be used as a porous sheet. Polyurethanes modified with cationic, anionic and aliphatic side chains may also be used. See, for example, U.S. Pat. No. 5,017,664. Polyurethanes may need to be dissolved in solvents such as dimethyl formamide, tetrahydrofuran, dimethyacetamide, dimethyl sulfoxide, or mixtures thereof.

The soft segments of these polyurethanes may contain any of the soft segments mentioned above, such as polytetramethylene oxide, polyethylene oxide, polypropylene oxide, polycarbonate, polyolefin, polysiloxane (i.e., polydimethylsiloxane), other polyether soft segments made from higher homologous series of diols, and mixtures of these soft segments. The soft segments may have amine end groups or alcohol end groups.

The hard segment may be formed from any of the diisocyantes listed above, such as 4,4'-diphenylmethane diisocyanate, tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The hard segment may be formed from one or more polyols. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, or mixtures thereof.

In addition, the polyurethanes may also be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

The porous polymeric sheet may contain a polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL -AL, and CARBOSIL polymers are thermoplastic elastomer urethane copolymers containing siloxane in the soft segment, and the percent siloxane in the copolymer is referred to in the grade name.

For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Patent Application Publication No. 2002/0187288 A1, which is incorporated herein by reference.

The porous polymer sheet may contain polytetrafluoroethylene or expanded polytetratfluoroethylene (ePTFE). Films or sheets of ePTFE are typically porous without the need for further processing. The structure of ePTFE can be characterized as containing nodes connected by fibrils. Porous ePTFE can be formed, for example, by blending PTFE with an organic lubricant and compressing it under relatively low pressure. Using a ram type extruder, the compressed polymer is then extruded through a die, and the lubricant is removed from the extruded polymer by drying or other extraction method. The dried material is then rapidly stretched and/or expanded at elevated temperatures. This process can provide for ePTFE having a microstructure characterized by elongated nodes interconnected by fibrils. Typically, the nodes are oriented with their elongated axis perpendicular to the direction of stretch. After stretching, the porous polymer is sintered by heating it to a temperature above its crystalline melting point while maintaining the material in its stretched condition. This can be considered as an amorphous locking process for permanently setting the microstructure in its expanded or stretched configuration. The structure and porosity of ePTFE is disclosed, for example, in U.S. Pat. Nos. 6,547,815 B2; 5,980,799; and 3,953,566; all of which are incorporated herein by reference. Structures of porous hollow fibers can be formed from PTFE, and these porous hollow fibers can be assembled to provide a cohesive porous sheet. Porous hollow fibers containing PTFE are disclosed, for example, in U.S. Pat. No. 5,024,671, which is incorporated herein by reference.

Polymers can be processed to be porous sheets using standard processing methods, including solvent-based processes such as casting, spraying and dipping, and melt extrusion processes. Extractable pore or hole forming agents can be used during processing to produce porous sheets. Examples of extractable pore forming agents include inorganic salts such as potassium chloride (KCl) and sodium chloride (NaCl), organic salts, and polymers such as poly (ethylene glycol) (PEG) and polyvinylpyrrolidone (PVP). Pore forming agents may have a particle size from about 10 µm to about 500 µm, from about 20 µm to about 100 µm, and from about 10 µm to about 40 µm. The amount of pore forming agent relative to the polymer may be from about 20 percent by weight (wt %) to about 90 wt %, and from about 40 wt % to about 70 wt %. These sizes and amounts of pore forming agents can provide for a high degree of porosity following extraction of the pore forming agent. The porosity can be from about 20 wt % to about 90 wt %, and from about 40 wt % to about 70 wt % of the final product.

Porous sheets may be in the form of a microporous, open-celled structure in which the pores are substantially interconnected. Microporous structures can be formed by extrusion of a mixture of polymer and one or more blowing agents. Microcellular polymeric foams can be produced by exposing the polymer to super-critical $CO_2$ under high temperature and pressure to saturate the polymer with the super-critical $CO_2$, and then cooling the polymer. Microcellular foams can be produced as described, for example, in U.S. Pat. Nos. 4,473,665 and 5,160,674, which are incorporated herein by reference. The foaming process can be carried out on extruded polymer tube by first dissolving an inert gas such as nitrogen or $CO_2$ under pressure into the polymer, and then forming microvoids by quickly decreasing the solubility of the gas in the polymer by changing the pressure or temperature, thus inducing thermodynamic instability. Examples of microporous polymeric structures are disclosed, for example, in U.S. Pat. No. 6,702,849 B1, which is incorporated herein by reference.

Porous THORALON can be formed by mixing the polyetherurethane urea, the surface modifying additive and a particulate substance in a solvent. Preferably the particulate is insoluble in the solvent, and the particulate may be any of a variety of different particulates or pore forming agents. For example, the solvent may be DMAC, and the particulate may be an inorganic salt. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting void-to-volume ratio can be substantially equal to the ratio of salt volume to the volume of the polymer plus the salt. The resulting pore diameter can also be substantially equal to the diameter of the salt grains.

The porous polymer sheet can have a void-to-volume ratio from about 0.40 to about 0.90. Preferably the void-to-volume ratio is from about 0.65 to about 0.80. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants-Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Patent Application Publication Nos. 2003/0114917 A1 and 2003/0149471 A1, both of which are incorporated herein by reference.

Extracellular Collagen Matrix (ECM)

In accordance with the invention, the graft material includes a polymeric sheet including holes, such as interstices or pores, and an extracellular collagen matrix disposed in the holes of the polymeric sheet. Preferably, the matrix is a comminuted extracellular collagen matrix.

Upon application of the graft material to the body of a subject, ECM in the graft material may undergo remodeling and induce the growth of endogenous tissues. The ECM of the graft material may serve as a matrix for, promote and/or induce the growth of endogenous tissue and undergo a process of bioremodeling. Common events related to this bioremodeling process may include widespread and rapid neovascularization, proliferation of granulation mesenchymal cells, biodegradation/resorption of implanted purified intestine submucosa material, and lack of immune rejection.

Studies have shown that ECM materials such as warm-blooded vertebrate submucosa may be capable of inducing host tissue proliferation, bioremodeling and regeneration of tissue structures following implantation in a number of in vivo microenvironments including lower urinary tract, body wall, tendon, ligament, bone, cardiovascular tissues and the central nervous system. Upon implantation, cellular infiltration and a rapid neovascularization may be observed and the submucosa material may be bioremodeled into host replacement tissue with site-specific structural and functional properties. This may occur as a result of one or more of the components of submucosa including, for example, glycosaminoglycans, glycoproteins, proteoglycans, and/or growth factors, including Transforming Growth Factor-α, Transforming Growth Factor-β, and/or Fibroblast Growth Factor 2 (basic).

ECM is the noncellular part of a tissue and consists of protein and carbohydrate structures secreted by the resident cells. ECM serves as a structural element in tissues. The extracellular matrix can be isolated and treated in a variety of ways. When harvested from the tissue source and fabricated into a graft material, the ECMs may be referred to as naturally occurring polymeric scaffolds, bioscaffolds, biomatrices, ECM scaffolds, extracellular matrix material (ECMM), or naturally occurring biopolymers. The ECM materials, though harvested from several different body systems as described below, all share similarities when processed into a graft material. Specifically, since they are subjected to minimal processing after they are removed from the source animal, they retain a structure and composition nearly identical to their native state. The host cells are removed and the scaffolds may be implanted acellularly to replace or repair damaged tissues while delivering therapeutic agents to the tissue.

The ECM for use in preparing graft materials can be selected from a variety of commercially available matrices including collagen matrices, or can be prepared from a wide variety of natural sources of collagen. Examples of these naturally occurring ECMs include tela submucosa, acellular dermis, cadaveric fascia, the bladder acellular matrix graft, and amniotic membrane (for review see Hodde J., Tissue Engineering 8(2):295-308 (2002)). In addition, collagen-based extracellular matrices derived from renal capsules of warm blooded vertebrates may be selected for use in preparing the graft materials of this invention. The extracellular matrices derived from renal capsules of warm blooded vertebrates were described in WO 03/02165, the disclosure of which is incorporated herein by reference.

Another type of ECM, isolated from liver basement membrane, is described in U.S. Pat. No. 6,379,710, which is incorporated herein by reference. ECM may also be isolated from pericardium, as described in U.S. Pat. No. 4,502,159, which is also incorporated herein by reference.

In addition to xenogenic biomaterials, autologous tissue can be harvested as well. Additionally elastin or elastin-like polypeptides (ELPs) and the like offer potential as a biologically active ECM. Another alternative would be to use allographs such as harvested native valve tissue. Such tissue is commercially available in a cryopreserved state.

In one example, the ECM for use in accordance with the present invention comprises the collagenous matrix having highly conserved collagens, glycoproteins, proteoglycans, and glycosaminoglycans, and/or growth factors, including Transforming Growth Factor-α, Transforming Growth Factor-β, and/or Fibroblast Growth Factor 2 (basic), in their natural configuration and natural concentration. In another example, the collagenous matrix comprises submucosa-derived tissue of a warm-blooded vertebrate, such as small intestine submucosa (SIS). Submucosal tissue can be obtained from various vertebrate organ sources (such as intestinal tissue) harvested from animals raised for meat production, including, for example, pigs, cattle and sheep or other warm-blooded vertebrates.

Juvenile submucosa tissue from warm blooded vertebrates, such as a porcine mammal, may also be used. Juvenile submucosal tissue was described in WO 04/22107, the disclosure of which is incorporated herein by reference.

The ECM present in the interstices of the polymeric sheet may be, for example, tela submucosa. "Tela submucosa" or "submucosa" refers to a layer of collagen-containing connective tissue occurring under the mucosa in most parts of the alimentary, respiratory, urinary and genital tracts of animals. Tela submucosa is a preferred source of ECM. Purified tela submucosa, a preferred type of ECM, has been previously described in U.S. Pat. Nos. 6,206,931, 6,358,284 and 6,666,892 as a biocompatible, non-thrombogenic material that enhances the repair of damaged or diseased host tissues. U.S. Pat. Nos. 6,206,931, 6,358,284 and 6,666,892 are incorporated herein by reference. The submucosa may be derived from intestine. The mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389, the disclosures of all are expressly incorporated herein.

The submucosa is preferably derived from the intestines, more preferably the small intestine, of a warm blooded vertebrate; i.e., small intestine submucosa (SIS). SIS is commercially available from Cook Biotech, West Lafayette, Ind. Preferred intestine submucosal tissue typically includes the tunica submucosa delaminated from both the tunica muscularis and at least the luminal portions of the tunica mucosa. In one example the submucosal tissue includes the tunica submucosa and basilar portions of the tunica mucosa including the lamina muscularis mucosa and the stratum compactum. The preparation of intestinal submucosa is described in U.S. Pat. No. 4,902,508, and the preparation of tela submucosa is described in U.S. patent application Ser. No. 08/916,490, both of which are incorporated herein by reference. The preparation of submucosa is also described in U.S. Pat. No. 5,733,337 and in 17 Nature Biotechnology 1083 (November 1999); and WIPO Publication WO 98/22158, dated 28 May 1998, which is the published application of PCT/US97/14855. Also, a method for obtaining a highly pure, delaminated tela submucosa collagen matrix in a substantially sterile state was previously described in U.S. Patent Application, Publication No. 20040180042, disclosure of which is incorporated by reference.

The stripping of the tela submucosa source is preferably carried out by utilizing a disinfected or sterile casing machine, to produce a tela submucosa which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the tela submucosa source can be employed, including, for example, delaminating by hand.

In this method, a segment of vertebrate intestine, preferably harvested from porcine, ovine or bovine species, may first be subjected to gentle abrasion using a longitudinal wiping motion to remove both the outer layers, identified as the tunica serosa and the tunica muscularis, and the innermost layer, i.e., the luminal portions of the tunica mucosa. The submucosal tissue is rinsed with water or saline, optionally sterilized, and can be stored in a hydrated or dehydrated state. Delamination of the tunica submucosa from both the tunica muscularis and at least the luminal portions of the tunica mucosa and rinsing of the submucosa provide an acellular matrix designated as submucosal tissue. The use and manipulation of such material for the formation of ligament and tendon grafts and the use more generally of such submucosal tissue constructs for inducing growth of endogenous connective tissues is described and claimed in U.S. Pat. No. 5,281,422 issued Jan. 25, 1994, the disclosure of which is incorporated herein by reference.

Following delamination, submucosa may be sterilized using any conventional sterilization technique including propylene oxide or ethylene oxide treatment and gas plasma sterilization. Sterilization techniques which do not adversely affect the mechanical strength, structure, and biotropic properties of the purified submucosa are preferred. Preferred sterilization techniques also include exposing the graft to ethylene oxide treatment or gas plasma sterilization. Typically, the purified submucosa is subjected to two or more sterilization processes. After the purified submucosa is sterilized, for example by chemical treatment, the matrix structure may be wrapped in a plastic or foil wrap and sterilized again using electron beam or gamma irradiation sterilization techniques.

Preferred submucosa may also be characterized by the low contaminant levels set forth in Table 1 below. The contaminant levels in Table 1 may be found individually or in any combination in a given ECM sample. The abbreviations in Table 1 are as follows: CFU/g=colony forming units per gram; PFU/g=plaque forming units per gram; µg/mg=micrograms per milligram; ppm/kg=parts per million per kilogram.

TABLE 1

| | First Preferred Level | Second Preferred Level | Third Preferred Level |
|---|---|---|---|
| ENDOTOXIN | <12 EU/g | <10 EU/g | <5 EU/g |
| BIOBURDEN | <2 CFU/g | <1 CFU/g | <0.5 CFU/g |
| FUNGUS | <2 CFU/g | <1 CFU/g | <0.5 CFU/g |
| NUCLEIC ACID | <10 µg/mg | <5 µg/mg | <2 µg/mg |
| VIRUS | <500 PFU/g | <50 PFU/g | <5 PFU/g |
| PROCESSING AGENT | <100,000 ppm/kg | <1,000 ppm/kg | <100 ppm/kg |

Purified submucosa may be further processed in a number of ways to provide ECM suitable for incorporation into the graft material of this invention.

It is also known that comminuted forms of submucosa can be prepared without loss of the submucosal tissue's ability to induce the growth of endogenous tissues. Comminuted submucosa compositions are prepared as solutions or suspensions or powder of intestine submucosa and comprise mechanically obtained submucosa or enzymatically treated submucosa. In one example, the submucosal tissue is mechanically and enzymatically treated to form a substantially uniform or homogenous solution. In another example, the submucosa is treated with a protease, such as trypsin or pepsin, or other appropriate enzymes for a period of time sufficient to solubilize the tissue and form a substantially homogeneous solution.

Preferably, the intestine submucosa starting material is mechanically comminuted by tearing, cutting, grinding, shearing and the like. Grinding the submucosa in a frozen or freeze-dried state is preferred although good results can be obtained as well by subjecting a suspension of pieces of the submucosa to treatment in a high speed (high shear) blender and dewatering, if necessary, by centrifuging and decanting excess water. The resultant fluidized intestine submucosa can be dried to form a submucosa powder. Thereafter, it can be hydrated, that is, combined with water or buffered saline and optionally other pharmaceutically acceptable excipients to form a intestine submucosa composition as a fluid having a viscosity of about 2 to about 300,000 cps at 25° C. The higher viscosity submucosal compositions can have a gel or paste consistency. The fluidized compositions can be sterilized using art-recognized sterilization techniques such as exposure to ionizing radiation. The preparation of fluidized forms of intestine submucosa is described in U.S. Pat. Nos. 5,275,826, 5,516,533, and 6,264,992, the disclosures of which are incorporated herein by reference.

The intestine submucosa may also be in the form of powder of submucosal tissues. In one example a powder form of submucosal tissue is prepared by pulverizing intestine submucosa tissue under liquid nitrogen to produce particles ranging in size from 0.01 to 1 mm in their largest dimension. The particulate composition is then lyophilized overnight, pulverized again and optionally sterilized to form a substantially anhydrous particulate composite. In another example, a powder form of submucosal tissue can be formed from fluidized submucosal tissue by drying the suspensions or solutions of submucosal tissue.

Both solid and fluidized forms of intestine submucosa have been found to induce endogenous remodeling processes including rapid neovascularization, proliferation of granulation mesenchymal cells, resorption of the submucosa tissue and absence of immune rejection. In vivo, submucosa tissue has been found effective to induce the proliferation and growth of cells/tissues with which it is in contact or which it replaces.

It is also possible to form large surface area constructs by combining two or more tela submucosa sections using techniques described in U.S. Pat. Nos. 2,127,903 and 5,711,969, which are incorporated herein by reference. Thus, a plurality of tela submucosa strips can be fused to one another, for example by compressing overlapping areas of the strips under dehydrating conditions, to form an overall planar construct having a surface area greater than that of any one planar surface of the individual strips used to form the construct.

Variations of the above-described processing procedures may be used to produce submucosa that may be incorporated into a polymeric sheet of the graft material. For example, the source tissue for the tela submucosa, e.g., stomach, whole intestine, cow uterus and the like, can be partially delaminated, treated with a disinfecting or sterilizing agent followed by complete delamination of the tela submucosa. Illustratively, attached mesentery layers, and/or serosa layers of whole intestine can be removed prior to treatment with the disinfecting agent, followed by delamination of remaining attached tissues from the tela submucosa. These steps may or may not be followed by additional disinfection steps, e.g., enzymatic purification and/or nucleic acid removal. Alternatively, the tela submucosa source can be minimally treated with a disinfecting or other such agent, the tela submucosa delaminated from the tunica muscularis and tunica mucosa, followed by a complete disinfection treatment to attain the desired contaminant level(s). All such variations and modifications of this step are contemplated.

The purified submucosa can be conditioned, as described in U.S. patent application Ser. No. 08/916,490, to alter the viscoelastic properties of the purified submucosa. The purified submucosa may be conditioned by stretching, chemically treating, enzymatically treating or exposing the matrix structure to other environmental factors. In one embodiment, the strips of purified tela submucosa may be conditioned by stretching in a longitudinal and/or lateral direction to a strain of no more than 20%. Strain is the percentage increase in the length of the material after loading.

In another embodiment, the purified submucosa may be conditioned by stretching the material longitudinally to a length longer than the length of the purified submucosa from which the ECM was formed. One method of conditioning the matrix by stretching involves application of a given load to the purified submucosa for three to five cycles. Each cycle consists of applying a load to the material for five seconds, followed by a ten second relaxation phase. Three to five cycles produces a stretch-conditioned material. The purified submucosa does not immediately return to its original size; it remains in a "stretched" dimension. Optionally, the purified submucosa may be preconditioned by stretching in the lateral dimension.

In one embodiment the purified submucosa may be stretched using 50% of the predicted ultimate load. The "ultimate load" is the maximum load that can be applied to the purified submucosa without resulting in failure of the matrix structure (i.e., the break point of the tissue). Ultimate load can be predicted for a given strip of purified submucosa based on the source and thickness of the material. Accordingly, one method of conditioning the matrix structure by stretching involves application of 50% of the predicted ultimate load to the purified submucosa for three to ten cycles. Each cycle consists of applying a load to the material for five seconds, followed by a ten-second relaxation phase.

The resulting conditioned purified submucosa has a resultant strain of less than 30%, more typically a strain from about 20% to about 28%. In one preferred embodiment, the conditioned purified submucosa has a strain of no more than 20%. The resultant conditioned purified submucosa can be used in the manner described below. The conditioning process and other relevant processes are described in U.S. Pat. No. 6,358,284 which is incorporated herein by reference.

Submucosa prepared using any variation of the processes described above, can be selectively disposed in a polymeric sheet to form a graft material of this invention as described below.

The ECM present in the interstices of a polymeric graft may be, for example, acellular dermis. Acellular dermis is composed of normal dermal tissue structures that remain after the cells are removed. Like other naturally occurring biopolymers, acellular dermis is rich in collagen type I. Acellular dermis also retains high levels of the type IV and type VII collagen composition of the native dermis (Medalie et al., ASAIO J. 42:M455 (1996)). In addition to collagen, the elastin content of the dermis is also retained during processing, leading to a graft construct with favorable elastic properties (Isch et al., J. Pediatr. Surg. 36:266 (2001)).

Acellular dermis may be harvested from either a pig or human cadaver skin. For example. Acellular dermis may be prepared according to Chaplin et al. (Chaplin et al., Neurosurgery 45:320 (1999)). Briefly, the epidermis may be removed by soaking the skin in sodium chloride (NaCl). Dermal fibroblasts and epithelial cells may be removed by incubation of the material in deoxycholic acid containing ethylenediaminetetraacetate (EDTA). The dermis may then be cryoprotected with a combination of maltodextrin and disodium-EDTA, and freeze dried until use (Chaplin et al., Neurosurgery 45:320 (1999)). When implanted as an acellular tissue graft, acellular dermis endothelializes repaired vascular structures (Inoue and Lleon, J. Reconstr. Microsurg. 12:307 (1996)), inhibits excessive wound contraction (Walden et al., Ann. Plast. Surg. 45:162 (2000)), and supports host cell incorporation and capillary ingrowth into the grafted site (Dalla et al., J. Pediatr. Surg. 45:162 (2000); and Medalie et al., ASAIO J. 42:M455 (1996)).

The ECM present in the interstices of a polymeric graft may be, for example, cadaveric fascia. The tensor fascia lata is thick band of connective tissue attaching the pelvis to the knee on the lateral side of the leg. Its muscular components at the hip join to thick connective tissues that help stabilize and steady the hip and knee joints by putting tension on the iliotibial band (IT band). The IT band, the distal section of the tensor fascia lata, may be harvested for the ECM of the graft material of this invention.

In its native state, the fascia lata tendon is composed of heavy, parallel bundles of type I collagenous fibers that are held together by extracellular matrix tissue. Between the bundles of fibers are fibroblasts, nerves, and blood vessels that supply the tendon with nutrients. Cadaveric fascia may be obtained by ethanol extraction followed by high-pressure washing with antibiotics. The extracted tissue may then be lyophilized and terminally sterilized with gamma irradiation. Intraoperatively, the graft material may be reconstituted with saline soak prior to use (Carbone et al., J. Urol. 165:1605 (2001)).

The ECM present in the interstices of a polymeric graft may be, for example, bladder acellular matrix. Bladder acellular matrix graft (BAMG) may be derived from a layer of the urinary bladder that is analogous to the submucosal tissue comprising the bulk of SIS biomaterial (Meezan et al, Life Sci. 17:1721 (1975)). In the native bladder, the bladder submucosa supports the mucosal structures and is secreted and maintained by fibroblasts. The normal function of ECM is to support the growth and differentiation of different mucosal cell types while maintaining a connective tissue structure that gives integrity to the bladder wall. Unlike the intestine submucosa, however, which is easily separated from the external muscle layers, the submucosa of the urinary bladder is intimately attached to the muscular bladder wall. Complete mechanical separation of the layers have proven tedious and difficult, and so attempts at rendering the bladder submucosa muscle-free have often resorted to chemical and/or enzymatic agents such as sodium hydroxide, sodium desoxycholate, sodium dodecyl sulfate (SDS), or deoxyribonuclease (Badylak et al., J. Pediatr. Surg. 35:1097 (2000); Merguerian et al., BJU Int. 85:894 (2000); Wefer et al., J. Urol. 165:1755 (2001); and Reddy et al., J. Urol. 164:936 (2000)).

In one processing method, whole bladders may be soaked in a Tris-EDTA solution for 48 hours followed by additional soaking in Tris-potassium chloride-EDTA solution containing Triton-X. Bladders may then be rinsed in Sorenson's phosphate buffer solution, incubated overnight with deoxyribonuclease and ribonuclease to remove cytoplasmic and nuclear material, and further extracted in a solution containing Tris and SDS. The extracted bladders may then be submerged in ethanol to remove any residual SDS, washed in phosphate buffer, and stored in refrigerated saline until use (Reddy et al., J. Urol. 164:936 (2000)).

Alternatively, bladder submucosa may be rendered acellular and sterile according to the methods used for SIS (Badylak et al., J. Pediatr. Surg. 35:1097 (2000)). The bladder layers may be mechanically separated and the resulting submucosa thoroughly rinsed in water to lyse the cells. The submucosa may be treated with peracetic acid and then rinsed in sequential exchanges of water and phosphate buffered saline to yield a neutral pH. It may then be sterilized using 2.5-mRad gamma irradiation and stored refrigerated until use.

The ECM present in the interstices of a polymeric graft may be, for example, amniotic membrane. The amniotic membrane forms the sac that encloses the embryo during pregnancy. It is extremely strong, 2-5 μg-thick tissue that may be used as a graft material in several tissue repair applications. In its native state, the epithelium of the amnion consists of a single layer of cells resting upon a relatively cell-free basement membrane ECM (Aplin et al., J. Cell Sci. 79:119 (1985)). This ECM consists of a microscopic substructure consisting of lamina rara and lamina densa that is comprised of several collagen types, including the fibrillar collagen types I and III, and the basal lamina collagen type IV (Aplin et al., J. Cell Sci. 79:119 (1985); and Lei et al., Biol. Reprod. 60:176 (1999)). At least one proteoglycan, decorin, has been identifies in near-term amniotic membrane (Meinert et al., J. Obstet. Gynecol. 184:679 (2001)), and has the glycosaminoglycan, hyaluronic acid (Meinert et al., J. Obstet. Gynecol. 184:679 (2001)). Several growth factors, including epidermal growth factor, several transforming growth factor isoforms, basic fibroblast growth factor, keratinocyte growth factor, and hepatocyte growth factor also have been identified and have been reported to be retained in the processed tissue matrix.

Amniotic membrane may be obtained at parturition and cleaned of blood with saline containing penicillin, streptomycin, amphotericin B, and clindamycin (Avila et al., Cornea 20:414 (2001)). It may be separated from chorion by blunt dissection, washed in sterile water, and treated by soaking for 3 hours in a 10% solution of trypsin to lyse the cells. The membrane may then be sterilized with gamma irradiation and frozen until clinical use (Young et al., Fertil. Steril. 55:624 (1991)).

It is also desirable that ECM be substantially free of any antibiotics, antiviral agents or any antimicrobial agents which may affect the inherent biochemical profile of the matrix and its efficacy upon implantation. One method of treating such tissue material includes rinsing the delaminated tissue in saline and soaking it in an antimicrobial agent, for example, as disclosed in U.S. Pat. No. 4,956,178, which is incorporated herein by reference. However, preferred processes avoid the use of antimicrobial agents and the like, which may affect the biochemical profile of the matrix and/or be unnecessarily introduced into the patient.

Preparation Of Graft Material Containing ECM

A polymeric sheet of a graft material may be coated, lined and/or impregnated with the ECM to provide the final graft product. The coating, lining and/or impregnation may be provided to reduce the porosity of the polymeric sheet at the time of implantation, thus avoiding or reducing blood loss through a porous graft. Such an ECM treatment can also contribute to the biocompatibility of the prosthesis material.

The term "impregnation" means providing for the presence of one or more components inside the polymeric sheet structure, in particular in the holes, such as interstices or pores of the polymeric sheet structure. Preferably, at least a substantial portion of the holes are open holes prior to treatment with ECM. More preferably at least the majority of the total hole volume is provided by open holes. Open holes extend from one surface of the graft material to another. Preferably at least a portion of the holes are filled with extracellular collagen matrix, such as comminuted intestine submucosa. The impregnation may partially or fully fill the interstices. Preferably the impregnation is provided as a layer at least partially covering the inner surface of the holes, while maintaining a sufficient openness (porosity) to allow migration of cells or precursors thereof into the graft material. The graft material may be impregnated with the ECM in a fluidized form or in a powder form. The ECM may be applied to the polymeric sheet directly at a desired location or may be pre-applied before application to the patient.

In one example, the ECM containing solution is applied to the graft sheet in any manner capable of uniformly impregnating the sheet. Fluidized ECM may be added to the polymeric sheet after preparation of the sheet, for example by soaking, dipping, spraying, painting, or otherwise applying the ECM to the sheet. Dipping and spraying are two conventional methods for impregnating the solution although dipping is preferred. In this method, the polymeric sheet may be dipped into a bath containing the fluidized ECM. The impregnated graft material is then removed from the bath and allowed to dry. During the drying step, the solvent evaporates leaving the ECM on the polymeric sheet of the graft material. The extent to which the fluidized ECM is impregnated into the polymeric sheet of the graft material is selected depending on the desired absorption capabilities of the graft material. Generally, the greater the amount of the ECM impregnated, the greater the absorption capability of the graft material and the longer the graft material may be retained at the desired location of on a patient's body.

Preferred methods of applying fluidized ECM to a polymeric sheet may include, for example vacuum impregnation and impregnation under pressure, which were described in U.S. Pat. No. 5,037,377. In one example of the vacuum impregnation process, the tubular polymeric sheets, which are highly porous in their unimpregnated form, are plugged at one end and are filled with fluidized ECM. The sheets are kept in a vessel which is evacuated to obtain a pressure differential in the physiological pressure range, preferably approximately 120 millimeters of mercury (mmHg). The pressure differential forces the fluidized ECM to flow through the holes of the polymeric sheet. Thereafter, the graft is incubated at 37 degrees centigrade, as noted above. Typically, the step of incubation is conducted in such a manner that the actual temperature of the graft material is maintained at 37 degrees centigrade for approximately twenty minutes. Thereafter, the grafts are dried for approximately twenty minutes. The steps of vacuum impregnation, incubation, and drying are repeated until tests with saline under physiological pressure (typically 120 Hgmm) show the graft materials to be sufficiently impervious to liquid. Usually, the steps of vacuum impregnation, incubation, and drying must be repeated approximately two to four times (most typically three times) to obtain substantially liquid impervious polymeric graft materials.

In one example of the process of impregnation under pressure, the tubular polymeric sheets are plugged at one end. Thereafter, fluidized ECM is placed under physiological pressure (usually 120 mmHg) into the tubular sheets. The pressure causes the fluidized ECM to flow through the polymeric sheet of the graft. After pressurization, the graft materials are incubated and dried as described in connection with the vacuum impregnation process. The process of impregnation under pressure, incubation, and drying is repeated until tests show that the graft is substantially impervious to liquid under physiological pressure. Usually, the procedure must be repeated two to four, most often three, times.

Another exemplary method of impregnating a sheet with an ECM includes mixing the comminuted ECM with the components of the sheet in a solvent prior to forming the sheet. In the example of THORALON, the polyetherurethane urea and siloxane-containing surface modifying additive can be mixed with comminuted ECM in a solvent. If the ECM is fluidized, it is preferable that the solvent not dissolve the ECM. A sheet can be formed by casting the mixture and evaporating the solvent. A sheet can also be formed by coagulating the mixture in a liquid that is a non-solvent for the polyetherurethane urea, the siloxane-containing surface modifying additive and the ECM. The sheet forming procedure can be optimized to insure that ECM is present in the holes of the polyetherurethane urea. This method may also be used to form a coating of a porous polymers containing ECM in the holes on an existing medical device.

When the ECM impregnated grafts are sufficiently impervious to liquid, they are immersed in a solution of glutaraldehyde for cross-linking and for deprivation of the antigenicity properties of the foreign animal proteins. In one example, treatment with 0.35 percent (by weight) or like concentration aqueous glutaraldehyde solution of approximately 7.4 pH is used to cross-link the ECM fibers with one another. Treatment with glutaraldehyde links the collagenous ECM fibers to one another, because it causes covalent chemical bond bridges to form between several protein chains of the fibers. The graft materials of the invention may then be stored and transported in glutaraldehyde or saline solution.

The ECM may also be incorporated into the sheet by binding it through photo-linking or other available means. Photo-linking, photo-activation, photo-polymerization, photo-crosslinking or photo-coupling refers to a process that is activated by light. A photo-activated step can be used to link the extracellular collagen matrix to a polymeric sheet to form graft materials of this invention. The photo-activation step may require the presence of a photoinitiator, examples of which include acetophenones, benzophenones, hydroxipropiophenones, thioxanthones, diphenyl ketones, benzoin and benzoin alkyl ethers, halogen substituted alkylaryl ketones, or quinone and anthraquinone derivatives.

The ECM may also be immobilized by allowing interaction between the ECM and the polymeric sheet under conditions where a stable covalent or non-covalent linkage forms, e.g., by photo-crosslinking the ECM if it and the surface comprise photo-activatable groups. "Stable" in this context refers to a linkage that is not disrupted during use of the fluidized ECM in a subsequent procedure, e.g., under washing or binding conditions. After immobilization, the surface can then be soaked, for example, in an aqueous buffer to remove non-covalently attached ECM and excess cross-linking components and/or reagents.

Graft materials containing ECM in the holes may be treated with antibiotics to prevent infection and to encourage healing, and may be used for certain kinds of prostheses, such as vascular grafts. An artificial graft made of such material can be filled with an antibiotic to prevent post-operation infections around the surgical field, with steroids to prevent rejection of the graft material, and with antimetabolites to prevent excessive scar formation around the graft. Likewise they may be filled with heparin, an anticoagulant, to prevent excessive clotting around the prosthesis.

According to the one embodiment of this invention, once the polymeric sheet of the graft material is filled with the ECM, the sheet will usually be dried before being worked or used. This can be done by freeze-drying, convection drying, or by microwave or other heating. This will leave the dry ECM in the holes of the polymeric sheet, which can then be worked to make the final product (which can be stored in dry form). Just before use, the graft material may be wetted with the appropriate liquid (water or buffered saline) to restore the ECM to its liquid form and make it readily diffusible out of the sheet. The product also can be used dry where it will be adequately wetted after application (due to the wetness of the site of use).

Therapy and Potential Uses of Graft Material Containing ECM

The graft materials containing ECM can be used, for example, for treatment of damaged or diseased tissues on a patient's body. The graft materials, upon placement on the damaged or diseased tissue on a patient's body, serve as a rapidly vascularized matrix for support and growth of new endogenous tissue. The graft material may be then remodeled (resorbed and replaced with autogenous differentiated tissue) and can assume the characterizing features of the tissue with which the graft material is associated at the site of placement.

In one example, the graft materials can be used in a method for promoting healing of tissues. The method includes contacting a tissue in need of healing with a graft material including a polymeric sheet comprising holes and having a comminuted ECM disposed in the holes of the polymeric sheet. For example, damaged or diseased portions of the patient's body may be repaired by placing a patch of a graft material including the polymeric sheet impregnated with comminuted extracellular collagen matrix. In another example, the graft material may be used to create bioresorbable wound dressings or band-aids. Wound dressings may be used as a wound-healing dressing, a tissue sealant (i.e., sealing a tissue or organ to prevent exposure to a fluid or gas, such as blood, urine, air, etc., from or into a tissue or organ), and/or a cell-growth scaffold. Such a wound dressing may protect the injured tissue and maintain a moist environment, and may be water permeable, easy to apply, non-toxic, non-antigenic, not require frequent changes and maintain microbial control.

Bioresorbable sealants and adhesives may be used in combination with the graft materials. Examples of bioresorbable sealants and adhesives include FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CyoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND™ which consists of 2-Octyl Cyanoacrylate produced by Dermabond (Ethicon); TISSUEGLU® produced by Medi-West Pharma; and VETBOND™ which consists of n-butyl cyanoacrylate produced by 3M.

Wound dressings may be used for soft tissue repair, including nerve repair, organ repair, skin repair, vascular repair, muscle repair, and ophthalmic applications. In other examples, wound dressings may be used to treat a surface such as, for example, a surface of the dermis and epidermis, the site of an anastomosis, a suture, a staple, a puncture, an incision, a laceration, or an apposition of tissue.

Wound dressings may be used in association with any medical condition that requires coating or sealing of a tissue. For example, bodily fluids may be stopped or minimized; barriers may be applied to prevent post-surgical adhesions, including those of the pelvis and abdomen, pericardium, spinal cord and dura, tendon and tendon sheath. Wound dressings may also be useful for treating exposed skin, in the repair or healing of incisions, abrasions, burns, inflammation, and other conditions requiring application of a coating to the outer surfaces of the body. Preferably, the graft material of this invention is used for wound healing and introduction of endogenous connective tissue in a patient in need of such treatment.

In a preferred embodiment, the graft materials may be used to manufacture medical devices, such as endoprostheses. Desirably, these medical devices are vascular or endovascular grafts, such as grafts, stents and combination stent-grafts. Useful vascular or endovascular grafts include those which are knitted or woven textiles or porous polymer sheets impregnated with ECM, such as comminuted SIS.

The functional vessels of human and animal bodies, such as blood vessels and ducts, occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Treatment of vascular conditions near a branch point with an endoluminal prosthesis can present a number of difficulties. A single, straight section of a tubular prosthesis may not be able to span the aneurysm or dissection and still maintain sufficient contact with healthy vascular tissue to secure the prosthesis and to prevent endoleaks. For example, most abdominal aortic aneurysms occur at or near the iliac bifurcation, and treatment with an endoluminal prosthesis requires the presence of prosthesis material in the main aorta and in the iliac branch arteries (Dietrich, E. B. *J. Invasive Cardiol.* 13(5):383-390, 2001). Typically, an endoluminal prosthesis for use near a bifurcation will have a main lumen body, for placement within the aorta, and two branch lumens extending from the main lumen body into the branch arteries.

One example of a bifurcated prosthesis is a single piece prosthesis. Such a unitary structure has a main tubular body and pre-formed leg extensions. The seamless structure provided by this configuration can minimize the probability of leakage within the prosthesis.

Another example of a bifurcated prosthesis is a modular system. In this system, one or both of the leg extensions can be attached to a main tubular body to provide the final prosthesis. Examples of modular systems are described in PCT Patent Application Publication WO98/53761 and in U.S. Patent Application Publication 2002/0198587 A1, which are incorporated herein by reference.

In one embodiment of this invention, an endoluminal prosthesis includes a tubular graft comprising a textile having fibers and interstices between the fibers, and having a comminuted ECM, such as comminuted intestine submucosa disposed in the interstices. The endoluminal prosthesis also includes a stent disposed about the graft material. The stent may be a self-expanding stent or a balloon expandable stent. The endoluminal prosthesis may also include a plurality of stents.

In another embodiment of this invention, an endoluminal prosthesis includes a tubular graft comprising a polymeric sheet comprising pores, and having a comminuted ECM, such as comminuted intestine submucosa disposed in the pores. The endoluminal prosthesis also includes a stent disposed about the graft material. The stent may be a self-expanding stent or a balloon expandable stent. The endoluminal prosthesis may also include a plurality of stents.

Figure 2:
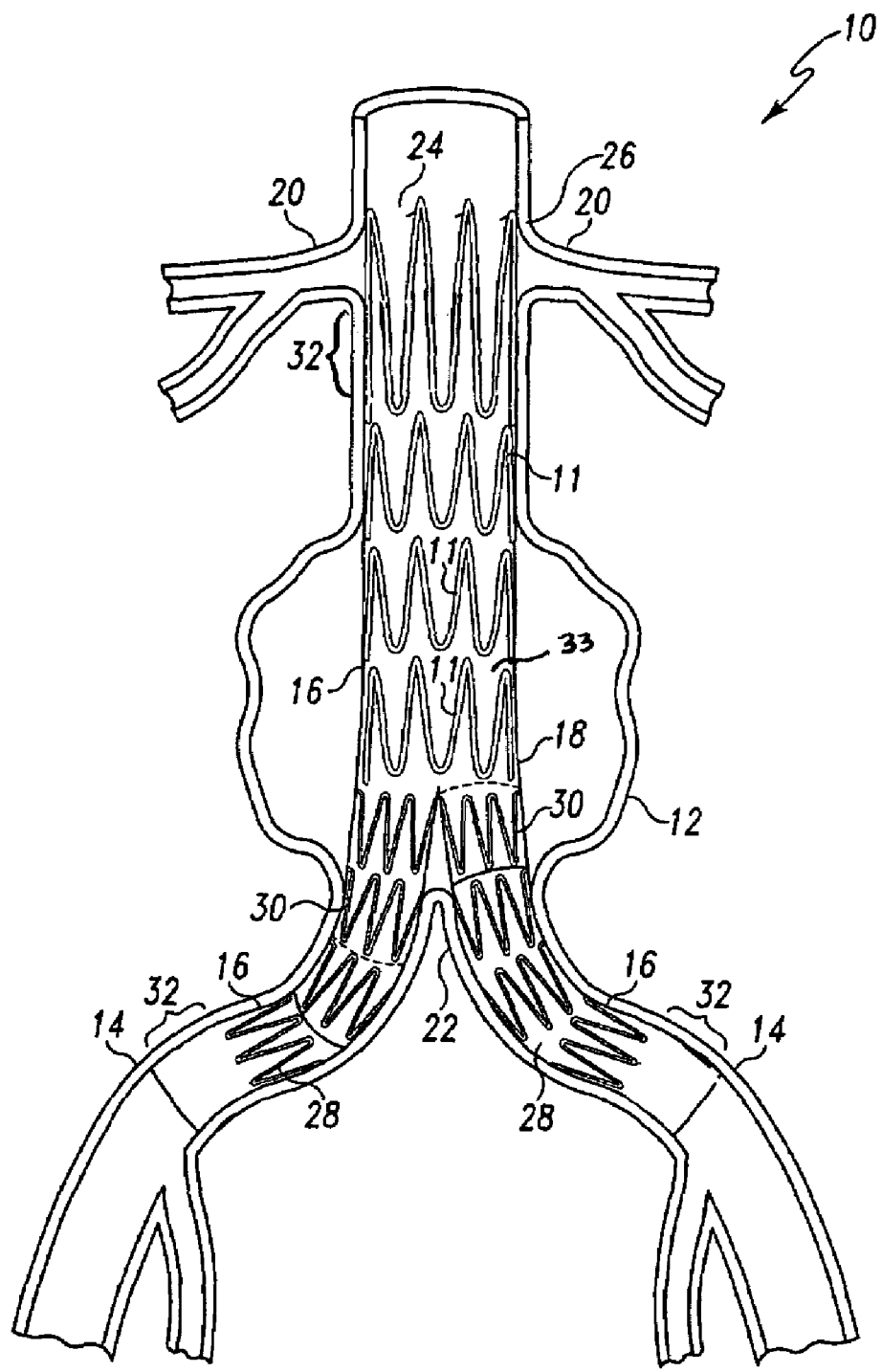
FIG. 2 shows a modular bifurcated aortic endoluminal prosthesis with polymeric material impregnated with extracellular collagen matrix, implanted within an aneurysmal aorta.

FIG. 2 shows an example of a modular bifurcated stent graft 10 deployed within an aneurysmal aorta 12 and both iliac arteries 14. Comminuted ECM is impregnated into the polymeric sheet 33. The prosthetic modules 16 that make up the stent graft 10 are generally tubular, so that the fluid can flow through the stent graft 10, and are preferably made of biocompatible polyurethane, polysiloxane, polyester, fluorinated polymer; or a textile, such as poly(ethylene terephthalate) or similar materials. The main body 18 extends from the renal arteries 20 to near the bifurcation 22. Multiple Z-stents 11 are sutured along the length of the stent graft 10. A suprarenal fixation stent 24 anchors the main body 18 to the healthier, preferably non-aneurysmal tissue 26 near the renal arteries. Two iliac extension modules 28 extend from the iliac limbs 30.

The stent graft 10 will preferably achieve a blood-tight seal at the contact regions 32 on both ends of the aneurysm 12, so that the aneurysm 12 will be excluded. In the particular embodiment shown in FIG. 2, the stent graft 10 contacts the vascular tissue below the renal arteries 20, around the bifurcation 22 and at the iliac limbs 30 and extensions 28. In this embodiment, a seal is preferably achieved that will help exclude the entire aneurysmal region and, as a result, the hemodynamic pressures within the aneurysm 12 may be reduced. These seals may be improved by the addition of extracellular collagen matrix to the polymeric sheet of the stent.

Figure 3:
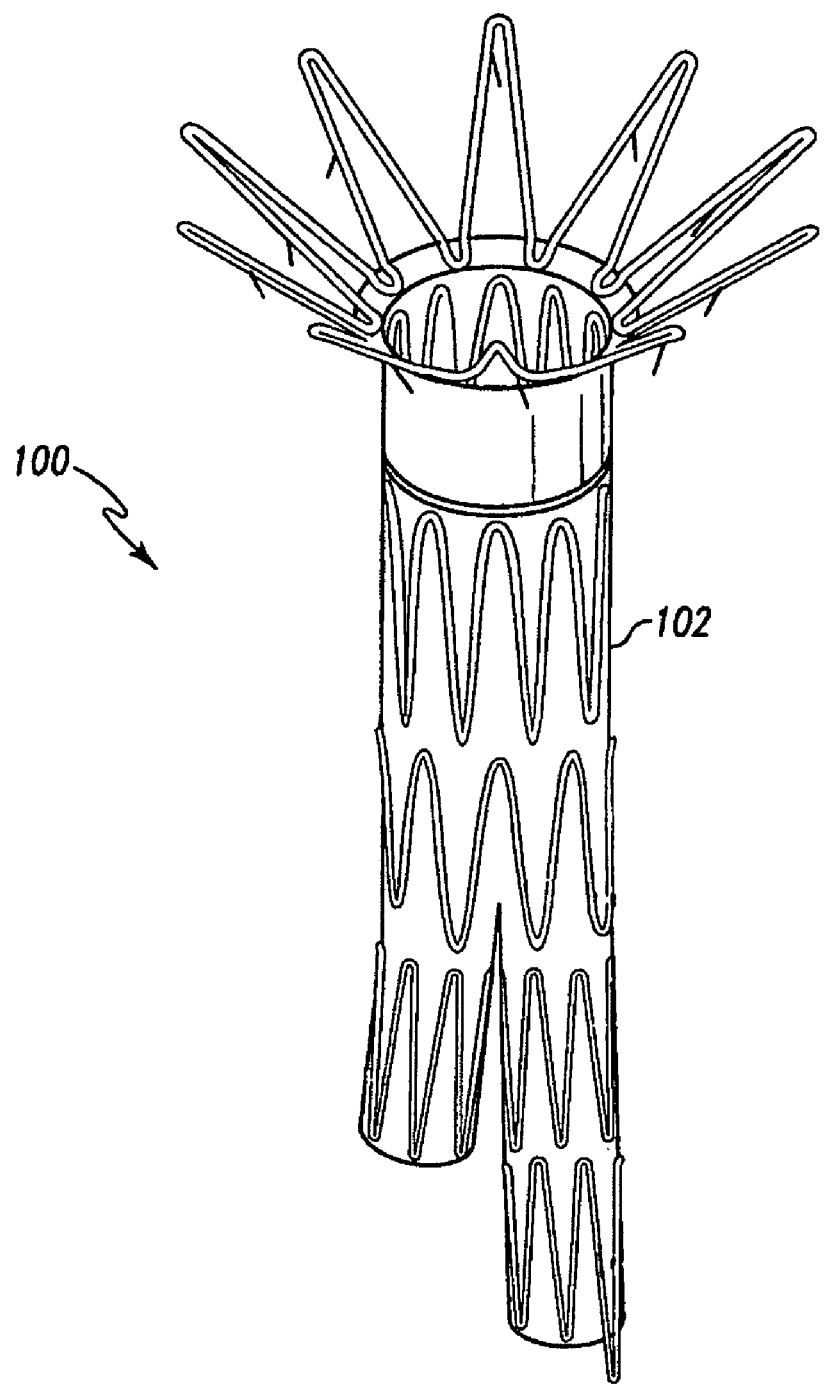
FIG. 3 shows a stent graft impregnated with extracellular collagen matrix.

FIG. 3 shows another example of a modular bifurcated stent graft 100. This figure shows a three-piece modular bifurcated stent graft 100 also designed for deployment into an aorta. Comminuted ECM is impregnated into the polymeric sheet 102.

Figure 4:
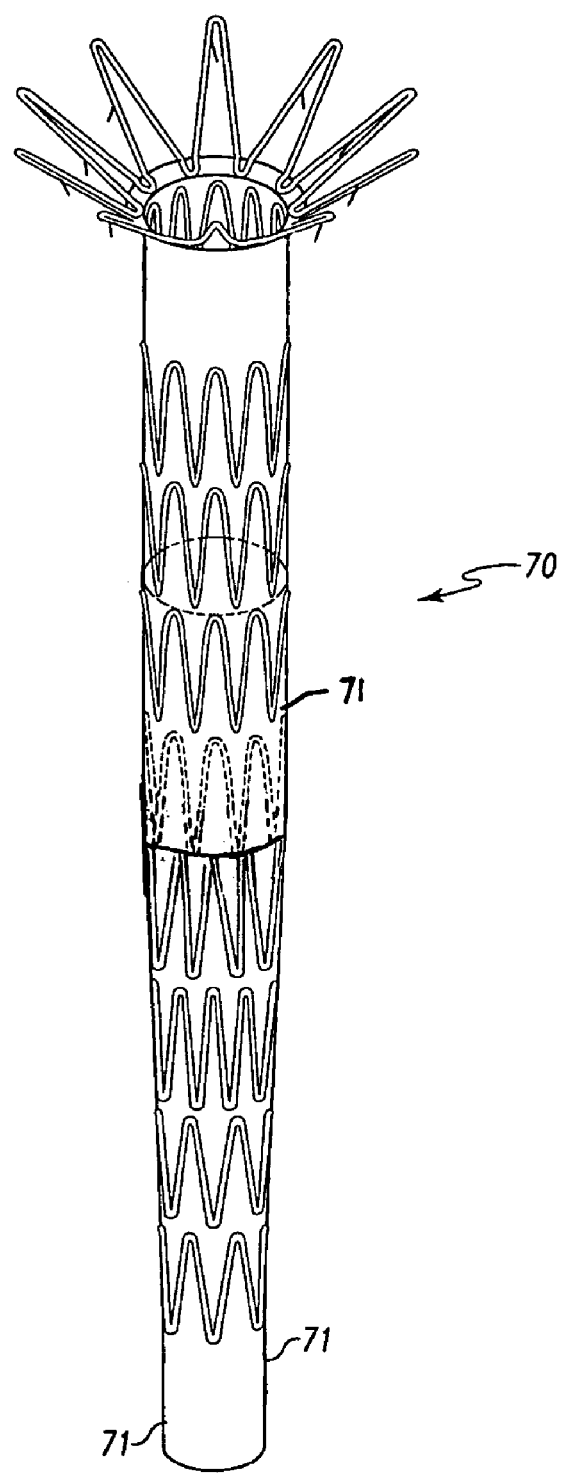
FIG. 4 shows an aorto-uniiliac endoluminal prosthesis with polymeric material impregnated with an extracellular collagen matrix material.

FIG. 4 shows a modular aorto-uniiliac stent graft 70 similar to that described in U.S. patent application Ser. No. 10/104,672, filed Mar. 22, 2002, which is incorporated herein by reference. The polymeric sheet 71 has extracellular collagen matrix incorporated into the interstices of the textile 71. The use of ECM can improve the seal and prevent migration of the graft 70.

In one aspect of the invention there is an endoluminal device that comprises a stent and a tubular graft supported by the stent. The graft has a proximal and a distal opening and comprises a polymeric sheet and an extracellular matrix material. The extracellular matrix material forms an exterior surface in at least one band adjacent at least one of the proximal and distal openings. When discussing the application of this invention to the aorta or other blood vessels, the term "distal" with respect to an abdominal device is intended to refer to a location that is, or a portion of the device that when implanted is, further downstream with respect to blood flow; the term "distally" means in the direction of blood flow or further downstream. The term "proximal" is intended to refer to a location that is, or a portion of the device that when implanted is, further upstream with respect to blood flow; the term "proximally" means in the direction opposite to the direction of blood flow or further upstream.

In one example, only a portion of a polymeric sheet used as a graft material for an endoluminal device comprises ECM, such as comminuted intestine submucosa disposed in holes of the polymeric sheet, forming ECM bands. The bands are preferably positioned at or near appropriate targets for fixation and/or encouraging circumferential apposition to the surrounding vessel. Examples of various devices that include ECM bands, were described in U.S. Application, entitled "Endoluminal Device with Extracellular Matrix Material and Methods;" U.S. application Ser. No. 10/644, 129; U.S. Provisional Application Ser. No. 60/404,662; and U.S. Provisional Application Ser. No. 60/572,806, which are incorporated by reference.

Figure 5:
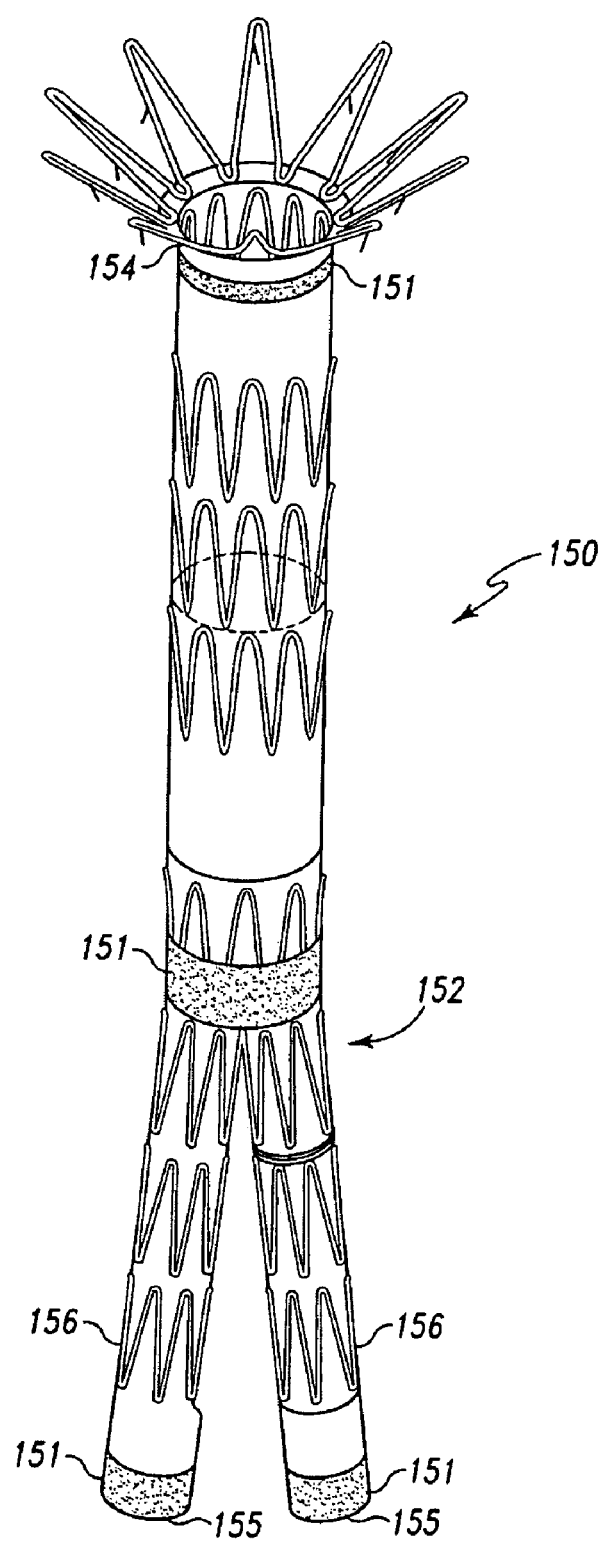
FIG. 5 depicts a modular bifurcated aortic stent graft with ECM bands, implanted within an aneurismal aorta.
Figure 6:
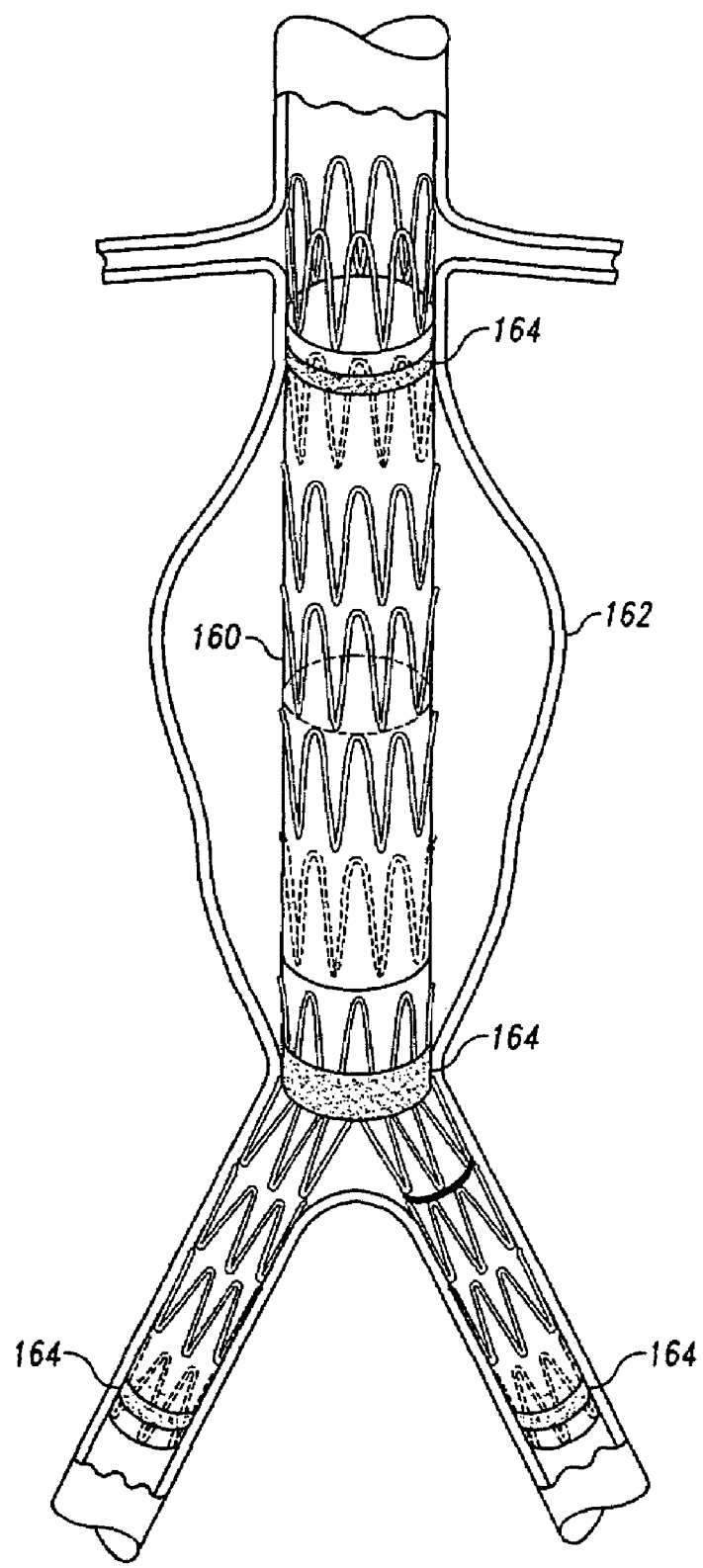
FIG. 6 depicts the stent graft similar to that of FIG. 5 after implantation within an aneurismal aorta.

For example, FIG. 5 shows a three-piece modular bifurcated stent graft 150 designed for deployment into an aorta. In this example, ECM 151 is incorporated near the bifurcation 152, as well as near the proximal opening 154 of the stent graft 150 and at the ends 155 of the iliac limbs 156. FIG. 6 shows a stent graft embodiment 160 similar to that of FIG. 5 after implantation. In FIG. 6, ECM bands 164 contact the surrounding vessel wall 162 at or near the external sealing zones.

Other uses of the graft material of this invention will be apparent to those of ordinary skill in the art. This invention is further illustrated by the following experimental examples, which should not be construed as limiting. The contents of all references, patents and published applications cited throughout this application are hereby incorporated by reference herein.

EXAMPLES

Example 1

Preparation of SIS Suspension

SIS specimens prepared as described above are minced or chopped into arbitrarily small pieces using tissue scissors, a single-edged razor blade, or other appropriate cutting implement. The specimens are placed in a flat bottom stainless steel container and liquid nitrogen is introduced into the container to freeze the specimens to prepare them for comminuting.

The frozen SIS specimens are then comminuted to form a coarse SIS powder. Such processing can be carried out, for example, with a manual arbor press with a cylindrical brass ingot placed on top of the frozen specimens. The ingot serves as an interface between the specimens and the arbor of the press. It is typically necessary to add liquid nitrogen periodically to the SIS specimens to keep them frozen.

Other methods for comminuting SIS specimens may be utilized to produce an SIS powder usable in accordance with the present invention. For example, SIS specimens can be freeze-dried and then ground using a manual arbor press or other grinding means. Alternatively, SIS can be processed in a high shear blender to produce, upon dewatering and drying, an SIS powder.

Further grinding of the SIS powder using a pre-chilled mortar and pestle can be used to produce consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

Example 2

Preparation of SIS Solution

SIS powder is sifted through a wire mesh into any convenient vessel. The powder is then subjected to proteolytic digestion to form a substantially homogeneous solution. In one embodiment, the powder is digested with 1 mg/ml of pepsin (Sigma Chemical Co., St. Louis, Mo.) in 0.1 M acetic acid, adjusted to pH 2.5 with HCl, over a 48 hour period at room temperature. The reaction medium is neutralized with sodium hydroxide to inactivate the peptic activity. The solubilized submucosa may then be concentrated by salt precipitation of the solution and separated for further purification and/or freeze drying to form a protease solubilized intestine submucosa in powder form.

The viscosity of fluidized submucosa compositions in accordance with this invention can be manipulated by controlling the concentration of the submucosa component and the degree of hydration. The viscosity can be adjusted to a range of about 2 to about 300,000 cps at 25° C. Low viscosity submucosa compositions are better adapted for intraarticular applications or applications within body cavities. Higher viscosity formulations, for example, gels, can be prepared from the SIS digest solutions by adjusting the pH of such solutions to about 6.0 to about 7.0. Gel forms of the present compositions, as submucosa suspensions or submucosa digest solutions, are typically preferred for impregnating polymeric graft materials of this invention.

Example 3

Preparation of Graft Material

Commercially available hollow Dacron™ (polyethylene terephthalate made by DuPont) fiber, 1.3 denier per filament T-727W (single-hole with 15% void), is used for vacuum-filling of the interstices between the fibers with fluidized SIS.

A 4.0 gram sample of 3.81 centimeters cut length is prepared by cutting the fiber with a sharp razor. The fiber diameter is 11.56 microns.

The fiber has tenacity of 4.5 grams per denier and elongation of 24.0%. It is important to cut the hollow fiber with sharp blades to keep fiber pores fully open.

The sample is next placed in a capetri dish and carefully pushed down with a small metal plate weighing approximately 20 grams to keep the sample down in the dish during vacuum operation. A fluidized SIS solution is poured into the dish until the fiber sample is completely submerged in the solution. After the sample dish is placed on a vacuum chamber, the vacuum pump (a Fisher Scientific Precision Direct-Drive Pump Model DD-90) is turned on for five minutes to obtain a vacuum of at least $1.0 \times 10^{-2}$ torr. Numerous air bubbles are observed escaping from the fiber sample at this time. (It is desirable that the air in the fiber pores or interstices be completely removed and a vacuum created.) Then the vacuum pump is turned off and the vacuum chamber is rapidly returned to atmospheric pressure. This causes the vacuum in the fiber interstices to be replaced with fluidized SIS. All interstices between the fibers are completely filled with the fluidized SIS in five minutes. These SIS-filled interstices between fibers look clear under an optical microscope while the air-filled interstices between fibers have dark streaks along the interstices because of refractive index differences.

The graft material is then washed thoroughly with distilled water to remove remaining SIS solutions from the surface of graft material.

More Preferred Embodiments

In one embodiment, the invention is a graft material, comprising a textile comprising fibers and interstices between the fibers; and a comminuted intestine submucosa disposed in the interstices of the textile. The textile is woven, non-woven or knitted. The interstices of the graft material comprise a maximum interstices spacing from about 1 micron to about 400 microns, or from about 1 micron to about 100 microns, or from about 1 micron to about 10 microns. The fibers comprise a synthetic polymer, wherein the synthetic polymer is selected from the group consisting of polyester, fluorinated polymer, and polyurethane. The polyester is polyethylene terephthalate. The fluorinated polymer is polytetrafluoroethylene. The fibers of the graft material have a denier from 0.5 denier per filament to 5 denier per filament and a fiber diameter from 1 micron to 5 millimeters. The intestine submucosa is a mechanically comminuted intestine submucosa or an enzymatically comminuted intestine submucosa. Preferably, the intestine submucosa is a small intestine submucosa.

In another embodiment, the invention is a method of making a graft material for implantation, comprising providing a textile made of fibers and having interstices between the fibers; providing a comminuted intestine submucosa; introducing the comminuted intestine submucosa into the interstices wherein the comminuted intestine submucosa remains in the interstices until after implantation. The fibers comprise a synthetic polymer, wherein the synthetic polymer is selected from the group consisting of polyester, fluorinated polymer, and polyurethane. The polyester is polyethylene terephthalate. The fluorinated polymer is polytetrafluoroethylene. The step of providing comminuted intestine submucosa comprises mechanically comminuted intestine submucosa or enzymatically comminuted intestine submucosa. The intestine submucosa is a small intestine submucosa. The step of providing comminuted intestine submucosa can also comprise fluidizing the comminuted intestine submucosa. The fluidizing the intestine submucosa comprises adjusting the viscosity of the fluidized intestine submucosa from about 2 to about 300,000 cps at 25° C. The step of introducing comprises immersing the textile in the fluidized intestine submucosa. The step of providing the comminuted intestine submucosa comprises providing the comminuted submucosa in a form of a powder. The step of introducing comprises depositing a layer of the comminuted intestine submucosa onto at least one side of the textile. The step of depositing comprises dipping, spraying or painting the textile with the comminuted intestine submucosa. The step of introducing comprises contacting one side of the textile with the comminuted intestine submucosa, and applying a vacuum to the opposite side of the textile. The step of introducing comprises immobilizing the comminuted intestine submucosa within the interstices, for example by contacting the graft material with glutaraldehyde. The comminuted intestine submucosa comprises a photoinitiator, and the immobilizing comprises exposing the graft material to a light source. The step of introducing further comprises drying the graft material.

In yet another embodiment the invention is a graft material, comprising a textile comprising fibers and interstices between the fibers; and a comminuted extracellular collagen matrix disposed in the interstices of the textile, wherein the matrix comprises at least one of highly conserved collagens, glycoproteins, proteoglycans, glycosaminoglycans, and growth factors. The extracellular collagen matrix is selected from the group consisting of small intestine submucosa, acellular dermis, cadaveric fascia, bladder acellular matrix, and amniotic membrane. The extracellular collagen matrix is a small intestine submucosa.

In yet another embodiment the invention is an endoluminal prosthesis, comprising a tubular graft material comprising a textile comprising fibers and interstices between the fibers, and having a comminuted intestine submucosa disposed in the interstices; and a stent disposed about the graft material. The prosthesis is a bifurcated prosthesis. The tubular graft material comprises a single proximal opening and first and second distal openings. The endoluminal prosthesis may further comprise a stent connected to and extending from the proximal opening. The stent may be is a self-expanding stent or a balloon expandable stent. The endoluminal prosthesis may also comprise a plurality of stents, wherein at least one of the stents is disposed on an interior of the tubular graft material or wherein at least one of the stents is disposed on an exterior of the tubular graft material.

In yet another embodiment the invention is a graft material, comprising a polymeric sheet comprising pores; and a comminuted intestine submucosa disposed in the pores. The polymeric sheet of the graft material comprises a polymer selected from the group consisting of polyesters, fluorinated polymers, polysiloxanes, polyurethanes, polyolefins, polyacrylonitrile, nylons, polyaramids and polysulfones. The polymeric sheet comprises a fluorinated polymer selected from the group consisting of polytetrafluoroethylene, expanded polytetrafluoroethylene and poly(vinylidene fluoride). The polymeric sheet may also comprise a polyurethane selected from the group consisting of polyetherurethanes, polyurethane ureas, polyetherurethane ureas, polyurethanes containing carbonate linkages and polyurethanes containing siloxane segments. The polymeric sheet may further comprise a polyetherurethane urea and a surface modifying agent comprising a siloxane. The polyetherurethane urea comprises soft segments and hard segments, wherein at least one soft segment comprises polytetramethylene oxide; and wherein at least one hard segment comprises the reaction product of 4,4'-diphenylmethane diisocyanate and ethylene diamine. The surface modifying agent includes a polyurethane comprising polydimethylsiloxane as a soft segment and the reaction product of 4,4'-diphenylmethane diisocyanate and 1,4-butanediol as a hard segment. The polymeric sheet comprises a void-to-volume ratio from about 0.40 to about 0.90, or from about 0.65 to about 0.80. The pores comprise an average pore diameter from about 1 micron to about 400 microns, or from about 1 micron to about 100 microns, or from about 1 micron to about 10 microns. The intestine submucosa is a mechanically comminuted or enzymatically comminuted. The intestine submucosa preferably is a small intestine submucosa.

In yet another embodiment, the invention is a graft material, comprising a polymeric sheet comprising pores; and a comminuted extracellular collagen matrix disposed in the pores. The matrix comprising at least one of highly conserved collagens, highly conserved glycoproteins, highly conserved proteoglycans, highly conserved glycosaminoglycans, and growth factors. The collagen matrix is selected from the group consisting of small intestine submucosa, acellular dermis, cadaveric fascia, bladder acellular matrix and amniotic membrane. The extracellular collagen matrix comprises small intestine submucosa.

In yet another embodiment, the invention is an endoluminal prosthesis, comprising a tubular graft material comprising a polymeric sheet comprising pores and a comminuted intestine submucosa disposed in the pores; and a stent disposed about graft material. The endoluminal prosthesis may be a bifurcated prosthesis. The tubular graft material comprises a single proximal opening and first and second distal openings. The endoluminal prosthesis may further comprise a stent connected to and extending from the proximal opening. The stent is a self-expanding stent or a balloon expandable stent. The endoluminal prosthesis may comprise a plurality of stents, wherein at least one of the stents is disposed on an interior of the tubular graft material or on an exterior of the tubular graft material. The polymeric sheet comprises a polymer selected from the group consisting of polyesters, fluorinated polymers, polysiloxanes, and polyurethanes. The polymeric sheet comprises a polyurethane selected from the group consisting of polyetherurethanes, polyurethane ureas, polyetherurethane ureas, polyurethanes containing carbonate linkages and polyurethanes containing siloxane segments. In one example, the polymeric sheet comprises a polyetherurethane urea and a surface modifying agent comprising a siloxane, wherein the polyetherurethane urea comprises soft segments and hard segments; wherein at least one soft segment comprises polytetramethylene oxide; and wherein at least one hard segment comprises the reaction product of 4,4'-diphenylmethane diisocyanate and ethylene diamine. The surface modifying agent comprises a polyurethane comprising polydimethylsiloxane as a soft segment and the reaction product of 4,4'-diphenylmethane diisocyanate and 1,4-butanediol as a hard segment. The polymeric sheet comprises a void-to-volume ratio from about 0.40 to about 0.90. The pores comprise an average pore diameter from about 1 micron to about 400 microns. The intestine submucosa is a mechanically comminuted intestine submucosa or an enzymatically comminuted intestine submucosa. Preferably the intestine submucosa comprises small intestine submucosa.

In yet another embodiment, the invention is a method of making a graft material for implantation. The method includes providing a polymeric sheet comprising pores; providing a comminuted intestine submucosa; and introducing the comminuted intestine submucosa into the pores, wherein the intestine submucosa remains in the pores until after implantation. The step of providing the comminuted intestine submucosa comprises fluidizing the comminuted intestine submucosa comprising adjusting the viscosity of the fluidized intestine submucosa from about 2 to about 300,000 centipoise at 25° C. The step of introducing comprises immersing the polymeric sheet in the fluidized intestine submucosa. The step of providing the comminuted intestine submucosa comprises providing the comminuted intestine submucosa is in the form of a powder. The step of providing the comminuted intestine submucosa comprises mechanically comminuting the intestine submucosa or enzymatically comminuting the intestine submucosa. The step of providing the comminuted intestine submucosa comprises providing small intestine submucosa. The step of introducing comprises depositing a layer of the comminuted intestine submucosa onto at least one side of the polymeric sheet by dipping, spraying or painting the polymeric sheet with the comminuted intestine submucosa. The step of introducing comprises contacting one side of the polymeric sheet with the comminuted intestine submucosa, and applying a vacuum to the opposite side of the polymeric sheet. The step of introducing further comprises immobilizing the comminuted intestine submucosa within the pores contacting the graft material with glutaraldehyde. The comminuted intestine submucosa comprises a photoinitiator, and the immobilizing comprises exposing the graft material to a light source. The step of introducing also comprises drying the graft material. The step of providing the polymeric sheet comprises providing a sheet comprising a polymer selected from the group consisting of polyesters, fluorinated polymers, polysiloxanes, and polyurethanes. The step of providing the polymeric sheet comprises providing a sheet comprising a polyurethane selected from the group consisting of polyetherurethanes, polyurethane ureas, polyetherurethane ureas, polyurethanes containing carbonate linkages and polyurethanes containing siloxane segments. The step of providing the polymeric sheet comprises providing a sheet comprising a polyetherurethane urea and a surface modifying agent comprising a siloxane. The step of providing the polymeric sheet comprises providing a sheet comprising a polyetherurethane urea comprising soft segments and hard segments wherein at least one soft segment comprises polytetramethylene oxide and at least one hard segment comprises the reaction product of 4,4'-diphenylmethane diisocyanate and ethylene diamine, and a surface modifying agent comprising a polyurethane comprising polydimethylsiloxane as a soft segment and the reaction product of 4,4'-diphenylmethane diisocyanate and 1,4-butanediol as a hard segment. The step of providing the polymeric sheet comprises providing a polymeric sheet comprising a void-to-volume ratio from about 0.40 to about 0.90. The step of providing the polymeric sheet comprises providing a polymeric sheet comprising pores having an average pore diameter from about 1 micron to about 400 microns.

In one embodiment, the invention is a method of making a graft material for implantation. The method comprises providing a polymeric sheet comprising holes, providing an ECM, and introducing the ECM into the holes of the polymeric sheet wherein the ECM remains in the holes until after implantation. The step of providing the ECM comprises providing a small intestine submucosa. The step of providing a small intestine submucosa comprises providing a comminuted small intestine submucosa, wherein the small intestine submucosa is a mechanically comminuted or enzymatically comminuted small intestine submucosa. The step of providing the comminuted small intestine submucosa comprises fluidizing the comminuted small intestine submucosa. The step of introducing comprises immersing the polymeric sheet in the fluidized small intestine submucosa. The step of providing the comminuted small intestine submucosa comprises providing the comminuted small intestine submucosa in a form of a powder. The step of introducing comprises depositing a layer of the ECM onto at least one side of the polymeric sheet by dipping, spraying or painting the polymeric sheet with the ECM. The step of introducing comprises contacting one side of the polymeric sheet with the ECM, and applying a vacuum to the opposite side of the polymeric sheet. The step of introducing comprises immobilizing the ECM within the holes by contacting the graft material with glutaraldehyde. The ECM comprises a photoinitiator, and the immobilizing comprises exposing the graft material to a light source. The step of introducing comprises drying the graft material.

It is to be understood that this invention is not limited to the particular methodology, protocols, cell lines, animal species or genera, constructs, or reagents described and as such may vary. It is also to be understood that the terminology used herein is for the purpose of describing particular embodiments only, and is not intended to limit the scope of the present invention which will be limited only by the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. A graft material, comprising:
   a polymeric sheet comprising holes; and
   a comminuted extracellular matrix (ECM) disposed in the holes of the polymeric sheet.

2. The graft material of claim 1, wherein the polymeric sheet is a textile selected from the group consisting of woven, non-woven, and knitted textiles.

3. The graft material of claim 2, wherein the textile comprises fibers and the holes are between the fibers.

4. The graft material of claim 3, wherein the fibers comprise a synthetic polymer.

5. The graft material of claim 4, wherein the synthetic polymer is polyethylene terephthalate.

6. The graft material of claim 1, wherein the polymeric sheet comprises a polymer selected from the group consisting of polyesters, fluorinated polymers, polysiloxanes, polyurethanes, polyolefins, polyacrylonitrile, nylons, polyaramids and polysulfones.

7. The graft material of claim 1, wherein the polymeric sheet further comprises a polyetherurethane urea and a surface modifying agent comprising a siloxane.

8. The graft material of claim 1, wherein the ECM is a small intestine submucosa.

9. A graft material of claim 1, wherein the comminuted extracellular matrix is impregnated in the holes of the polymeric sheet.

10. An endoluminal prosthesis, comprising:
    a tubular graft material comprising a polymeric sheet comprising holes, and a comminuted extracellular matrix (ECM) disposed in the holes of the polymeric sheet; and
    a stent disposed about the graft material.

11. The endoluminal prosthesis of claim 10, wherein the ECM is a small intestine submucosa.

12. The endoluminal prosthesis of claim 10, wherein the prosthesis is a bifurcated prosthesis.

13. The endoluminal prosthesis of claim 10, wherein the tubular graft material comprises a single proximal opening and first and second distal openings.

14. The endoluminal prosthesis of claim 13, further comprising a stent connected to and extending from the proximal opening.

15. The endoluminal prosthesis of claim 10, wherein the stent is a self-expanding stent or a balloon expandable stent.

16. The endoluminal prosthesis of claim 10, further comprising a plurality of stents.

17. The endoluminal prosthesis of claim 10, wherein the comminuted extracellular matrix is impregnated in the holes of the polymeric sheet.

* * * * *